(12) United States Patent
Miller

(10) Patent No.: US 6,562,326 B1
(45) Date of Patent: May 13, 2003

(54) TOPICAL COMPOSITION FOR BURN HEALING

(76) Inventor: Bruce W. Miller, 4450 Gulf Blvd. 316#, St. Pete Beach, FL (US) 33706

( * ) Notice: Subject to any disclaimer, the term of this patent is extended or adjusted under 35 U.S.C. 154(b) by 1226 days.

(21) Appl. No.: 08/695,393

(22) Filed: Aug. 12, 1996

(51) Int. Cl.[7] ................................................ A61K 7/075
(52) U.S. Cl. ................................ 424/70.19; 424/70.22; 424/70.27; 514/299; 514/535; 514/817
(58) Field of Search .................................. 514/299, 535, 514/817; 424/70.19, 70.22, 70.27, 70.31

(56) References Cited

U.S. PATENT DOCUMENTS 4,946,870 A * 8/1990 Partain, III et al. ......... 514/777
5,650,157 A * 7/1997 Bockow ...................... 424/401

FOREIGN PATENT DOCUMENTS

EP    0 446 225 B1 * 3/1993

* cited by examiner

*Primary Examiner*—Sheela Huff
(74) *Attorney, Agent, or Firm*—Philip M. Weiss; Weiss & Weiss

(57) ABSTRACT

A method of treating skin includes applying a topical composition to an affected area of skin, such as a burn, irritation, blister, rash or other similar skin condition. The topical composition has as the active ingredients an anesthetic and a surfactant. The anesthetic is preferably tetracaine in a concentration of from about 1% to 2% by weight and the surfactant is preferably sodium lauryl sulfate in a concentration of from about 0.5% to about 5.0% by weight.

9 Claims, No Drawings

TOPICAL COMPOSITION FOR BURN HEALING

BACKGROUND OF THE INVENTION

The present invention relates to a topical composition having medicinal properties, in particular, it relates to a topical composition for use in treating burns, scalds, blisters, rash, scabs or other skin conditions experienced by human skin.

Burns cause inflammation of the skin, pain and swelling and may result in scabbing and scarring. Skin burns are a complex inflammatory process causing dyskeratotic cells, spongiosis, vacuolation of keratinocytes and edema from capillary leakage, 12 to 24 hours after exposure to light or high temperature. In addition to redness and pain, blisters may develop and scabs and scars may result.

Known treatments for burns are limited in efficacy. The topical use of anti-inflammatory agents to alleviate inflammation resulting from burns is known. Compositions containing steroidal anti-inflammatories, non-steroidal anti-inflammatories, as well as "natural" anti-inflammatories, such as extract of the plant aloe vera, have been used.

In the past there have been many salves for the topical treatment of human skin. Although most known salves or ointments have medicinal or soothing characteristics, they do not aid in preventing blistering or scabs and reducing or eliminating scarring of the skin tissue or have an immediate effect on the reduction of pain.

SUMMARY OF THE INVENTION

The preferred embodiments of the present invention provide topical compositions and methods of use thereof for the alleviation of the symptoms associated with burns of human skin. The preferred embodiments of the present invention also provide a method of applying topical compositions for alleviation of the symptoms of burns with no side effects and relief from inflammation and pain normally associated with burns while preventing or reducing scabbing and scarring of the skin.

The preferred embodiments of the present invention provide a topical composition for reducing the symptoms of burns and shortening time required for healing. The composition preferably comprises a therapeutically effective amount of a combination of an anesthetic and a surfactant. Varying amounts of anesthetic and surfactant are preferably used to achieve efficacious results, e.g., for anesthetic concentrations of from about 0.05% to 25% by weight, preferably 0.25% to 10% by weight, and most preferably 1% to 5% by weight, and for surfactant, concentrations of from about 0.05% to 50% by weight, 1% to 10% by weight, and 0.5% to 5% by weight.

In preferred embodiments, the anesthetic is preferably selected from the group consisting of esters, amides, ethers, and combinations thereof and, in particular, topical anesthetics and other anesthetics which may be formulated in accordance with the preferred embodiments of the present invention and applied topically, including procaine, chloroprocaine, tetracaine, propoxycaine, benzocaine, cocaine, proparacaine, bupivacaine, dibucaine, etidocaine, lidocaine, mepivacaine, prilocaine, dyclonine, promazine and combinations thereof.

The surfactant is preferably selected from the group consisting of anionic, nonionic, and cationic surfactants and combinations thereof. Suitable ionic surfactants include anionic surfactants such as monovalent salts, e.g., sodium and potassium salts of alkyl, aryl and alkyl-aryl sulfates and sulfonates, particularly those with from about 8 to 22 carbon atoms, and cationic surfactants, such as quaternary ammonium salts. Suitable non-ionic surfactants include polyethylene oxide adducts of fatty alcohols, e.g., alkylated polyoxyethylenes, alkylated polyoxyethylene-polyoxypropylene copolymers, and the surfactant nonoxynol.

The surfactant and the anesthetic are preferably formulated together in a pharmaceutically acceptable topical carrier, which may comprise one of a number of known acceptable forms. Suitable topical carriers include known aqueous carriers and oleaginous carriers.

The composition may also contain one or more additional agents, including antimicrobial agents, anti-viral agents, anti-fungal agents, buffering agents, antioxidants, preservatives, coloring agents, fragrances, lubricants, moisturizers, sunscreens, drying agents and the like and, more specifically, may include ingredients such as stearic acid, lauramide DEA, borax, eucalyptus oil, beeswax, preservative and methylparaben.

The preferred embodiments of the present invention also provide a method for reducing the symptoms of burns including swelling, redness, pain, and scarring while also decreasing time required for healing by topically administering a composition according to a preferred embodiment of the present invention to a burn area, preferably at least about once every twelve hours and, more preferably, about every four hours depending upon the amount of pain. The composition is preferably applied to the burn area daily for maximum benefit. Relief is almost immediate, and is characterized by decreased pain, swelling, and more rapid healing as compared with untreated burns. In addition, the topical administration of the composition reduces or prevents scabbing and scarring of the skin affected by the burn.

These and other elements, features and advantages of the preferred embodiments of the present invention will be apparent from the following detailed description of the preferred embodiments of the present invention.

DETAILED DESCRIPTION OF PREFERRED EMBODIMENTS

The preferred embodiments of the present invention provide a method for applying a topical composition to treat a skin burn, the composition having two essential components, a topical or local anesthetic and a surfactant. An anesthetic and a surfactant are preferably added to a conventional carrier, such as, a cream, ointment, solution or gel containing appropriate stabilizers, buffers and preservatives for topical application to the burn area.

The topical anesthetics of the preferred embodiment of the present invention are esters, ethers or amides and include the following anesthetics which may be included in the compositions according to the preferred embodiments of the present invention. Esters include Tetracaine, Benzocaine, Proparacaine, Procaine, Cocaine (not a legal drug in the United States) and Propoxycaine. Amides include Dibucaine and Lidocaine. Ethers include Dyclonine and Promazine.

There are other anesthetics used for injection, e.g., spinal anesthesia, which are not usually listed as topicals but are expected to work well on burns where intact skin does not present a barrier. Some examples of these anesthetics are: Chloroprocaine, Bupivacaine, Etidocaine, Mepivacaine and Prilocaine.

In a preferred embodiment, the anesthetic is tetracaine (either as the hydrochloride or other salt or as the free base).

Tetracaine is a preferred anesthetic because the anesthetic penetrates skin most effectively, and it is on the FDA monograph list which allows marketing as an over-the-counter (OTC) product for fever blisters and cold sores at concentrations up to 2% by weight.

In a preferred embodiment, the anesthetic is combined with a carrier in a concentration range of between approximately 1% and 2% by weight; however, the anesthetic may be present in varying concentrations, for example, between approximately 0.05% and 25% by weight, between approximately 0.25% and 10% by weight, between approximately 0.5% and 10% by weight, and between approximately 1% and 5% by weight. The exact dose of anesthetic to be employed in a given formulation will depend on a number of factors such as the particular anesthetic to be employed. For example, in compositions containing benzocaine as the anesthetic, an exemplary preferred dose range is between approximately it and 20% by weight, in compositions containing lidocaine, an exemplary preferred dose range is between approximately 1% and 20% by weight and in compositions containing tetracaine an exemplary preferred dose is approximately 0.5%.

In addition to the local anesthetic, the compositions used in the method of the preferred embodiment of the invention also contain a therapeutically effective amount of a surfactant. Surfactants have been discovered to have a very low degree of toxicity and work to speed the healing process relating to burn areas. The surfactant facilitates penetration of the anesthetic, enhancing the effectiveness of the individual compounds to facilitate healing.

In a preferred embodiment, the surfactant in the formulation is sodium lauryl (or dodecyl) sulfate, also referred to as "SLS", a common surfactant found in toothpaste and other cosmetic preparations, known to "unfold" the tertiary structure of proteins. Sodium lauryl sulfate is an anionic surfactant with a negatively charged sulfate group. Sodium lauryl sulfate is also capable of penetrating intact skin very effectively. Other monovalent sulfur-containing surfactants, e.g., the sodium or potassium alkyl, alkyl-aryl, and aryl sulfates or sulfonates can be used in accordance with a preferred embodiment of the invention.

In addition, cationic surfactants may be used, alone or in combination with SLS. An example is trimethyldodecylammonium chloride, a positively charged quaternary ammonium complex which has antimicrobial characteristics. Other quaternary salts, with and without long chain moieties to provide surface activity, may also be useful.

Nonionic surfactants, the most common being nonoxynol, may also be useful. Common nonionic surfactants include nonoxynol, polyoxyethylenes, polyoxyethylene-polyoxypropylene copolymers and alkyl sorbitols.

In a preferred embodiment, the surfactant is preferably combined with a carrier in a concentration range of between approximately 0.5% to 2%, by weight. However, the surfactant may be present in a concentration of between approximately 0.1% to 10% by weight. The selected surfactants may also be combined in varying concentration ranges, for example, between approximately 0.1% to 20% by weight, between approximately 0.05% to 50% by weight, between approximately 1.0% and 10% by weight and between approximately 0.5% and 5.0% by weight.

The composition can also contain antimicrobials, including antibiotics, antifungals, and other anti-viral compounds which may complement or supplement the activity of the basic composition. Suitable antibiotics include tetracycline, polymyxin B or other common antibiotics used in topical compositions, especially over-the-counter formulations. Examples of useful antifungals include tolnaftate and micatin. Examples of anti-virals include interferon, either natural or recombinant, as well as nucleoside analogs, e.g., Acyclovir. Counter-irritants such as camphor and menthol, drying agents such as benzyl alcohol, resorcinol and phenol, and astringents such as zinc sulfate and tannic acid can also be added to the composition as can other types of agents such as sunscreens, emollients, preservatives, fragrances, antioxidants, color additives, lubricants, moisturizers or drying agents. For example, a sunscreen, e.g., PABA, can be added to the formula since it is known that burns can be caused by ultraviolet radiation.

The composition used in the method according to the preferred embodiments can be prepared in almost any relatively inert topical carrier. Generally, the formulation could take several forms, e.g., cream, gel, spray, ointment, "Chapstick" and solution forms. Each of these formulations may contain the two active ingredients as well as microorganism growth inhibitors (preservatives). Many such carriers are routinely used and can be obtained by reference to pharmaceutical texts. Examples include polyethylene glycols (PEG), polypropylene copolymers (Pluronics), and some water soluble gels.

The preferred carrier is an emulsified cream, but other common carriers such as certain petrolatum or mineral oil-based ointments in which the surfactant and anesthetic are dispersible can be substituted. For example, one suitable cream formulation used in animal studies and clinical experiments is described below:

| COMPONENT | PERCENT (approximate) |
| --- | --- |
| Deionized water | 69 |
| Stearic Acid | 22 |
| Sodium lauryl sulfate | 1 |
| Beeswax | 1 |
| Tetracaine | 2 |
| Borax | 0.4 |
| Lauramide DEA | 3.6 |
| Methylparaben | 0.3 |
| Eucalyptus Oil | 0.03 |

At this time, the preferred composition determined through actual testing to be most effective in enhancing healing of burns is: (all percents are by weight):

methylparaben, 0.25% (0.25% to 0.5%)

borax, 0.5% (0.3% to 0.6%)

lauramide DEA, 4% (3.0% to 4.0%)

stearic acid, 20% (15% to 25%)

beeswax, 0.8% (0.5% to 1.5%)

tetracaine, 1.8% (1% to 2%)

sodium lauryl sulfate, 0.8% (0.1% to 3%)

eucalyptus oil 0.025% (0.01% to 0.05%)

PCMX 0.4% (0.3% to 0.5%)

water to a total of 100%

Gels, i.e., thickened aqueous or alcoholic solutions, containing the active ingredients and stabilizers may be clear and/or colored with suitable dyes. Suitable thickeners may include carboxymethylcellulose, polyvinyl-pyrrolidone or polyacrylic acid salts.

Hydrophilic or hydrophobic ointments may be employed as carriers. However, hydrophobic ointments, such as Vaseline, which are based upon hydrocarbon and wax derivatives may not be as efficacious as the hydrophilic ointments because they may impede penetration into the skin. Hydrophilic ointments such as those based upon propylene glycol, polyalkylene glycols, and the Pluronics are therefore preferred for ointment formulations. Propylene glycol, as a base, is preferable to polyethylene glycol.

"Chapstick" formulations may be employed in situations, e.g., for treatment of burns, where ease of application is a primary objective.

Solutions, i.e., dilute aqueous preparations containing active ingredients and preservatives but without substantial concentrations of thickeners, can be sprayed upon the affected surface with an aerosol pump. This type of delivery may be of value for treating larger areas of painfully sensitive skin.

In most cases, it is preferred that the pH of the carrier containing the active ingredients is adjusted to a pH of about 6 to 7, using, as buffering agents, ingredients such as borax although other acceptable buffering agents could be used.

Additional additives may include antioxidants, fragrance, color, water, preservatives (either antioxidants or antimicrobials), lubricants, moisturizers, or drying agents.

According to a preferred embodiment of the present invention, the composition is preferably applied to the burn area one to six times daily, most preferably beginning immediately after the burn occurs. A liberal amount of the composition is preferably applied to cover the burn area, however, just a thin coating is required to reduce pain, redness and swelling and prevent or reduce blistering, scabbing and scarring.

Examples 1–6 are accounts of persons who have used a composition of a preferred embodiment of the present invention to treat burns.

EXAMPLE 1

A patient received a burn caused by heat emitting from an engine at a temperature of 350 degrees fahrenheit. The burn caused pain and a reddened area on the arm. The patient immediately applied a thin layer of a composition according to a preferred embodiment of the present invention (SLS and Tetracaine) to the reddened area. Within 60 seconds, the pain was eliminated. Within a few hours the redness was eliminated. The patient did not experience any pain except for the initial burn, and no scarring or blistering resulted.

EXAMPLE 2

The same patient as in Example 1 later burned himself as the result of touching a heated gel pack in a microwave oven. The finger area which had touched the gel turned white in color. The patient had developed a second degree burn. A thin layer of the inventive composition was placed on the burn area. Within 60 seconds the pain was approximately 60–70% under control. The pain was still lingering three minutes later.

A second thin layer of inventive composition was applied to the burn area, and within 60 seconds the remaining pain was gone. Fifteen to twenty minutes later the whiteness of the burned area on the fingers turned to a deep red. A few hours later, the redness was eliminated. After the second application of the composition, no feeling of pain existed. There was no scarring and no blistering.

The next morning the patient immersed himself in a 105–106° F. bath. The patient immersed his formerly burned hand in the bath with no effects. Usually when one is burned, if one applies heat to the burned area, pain returns to that area. Here, the patient felt no such pain.

EXAMPLE 3

A patient had scalded herself with hot water from a bath. The patient dried herself off and immediately applied the inventive composition to the burn area. Within 30 minutes, all of the pain and redness was gone, there was no scarring and no blistering.

EXAMPLE 4

A patient burned herself by placing her finger in boiling water. The finger was blistered and painful. The inventive composition was applied to her finger. By the next day the person experienced no further pain, the blisters were gone and there was no scarring.

EXAMPLE 5

A patient had been overexposed to the sun. That evening his skin was very red. The inventive composition was applied to the patient's face. Within a few hours the patient's face color had returned to normal, which contrasted with the red of the skin which had not had the inventive composition applied.

EXAMPLE 6

A patient had been burned when a lamp fell onto her arm. She immediately applied an over-the-counter burn medicine. This however did not stop the burning and a scab formed. Approximately one hour later the patient applied a small amount of the inventive composition on her blistered skin. Almost instantly, the burning and throbbing stopped. In the morning the burn did not hurt and all of the surrounding redness was gone. For the next few mornings the patient reapplied the inventive composition. When the scab initially formed in the burned area before application of the inventive composition fell off, there was no scar or no marks resulting from the burn.

While the invention has been described in detail and with reference to specific preferred embodiments thereof, it will be apparent to one skilled in the art that various changes and modifications can be made therein without departing from the spirit and scope thereof.

What is claimed is:

1. A method for treating burns comprising topically administering to a burn area a composition consisting essentially of the combination of:

(a) tetracaine, in a concentration of from about 1% to 2% by weight; and (b) sodium lauryl sulfate in a concentration of from about 0.5% to about 5.0% by weight and wherein said combination is administered in a pharmaceutically acceptable carrier for topical administration.

2. The method of claim 1 wherein said sodium lauryl sulfate has a concentration of about 1% by weight.

3. The method of claim 1 wherein said composition is applied to the burn area at least once every twelve hours.

4. A method for treating burns comprising topically administering to a burn area a composition consisting essentially of the combination of:

(a) an anesthetic selected from the group consisting of esters, amides and ethers; and (b) a surfactant selected from the group consisting of anionic, nonionic and cationic surfactants.

5. The method of claim 4 wherein the anesthetic is approximately 0.05% to 25% by weight of said composition.

6. The method of claim 4 wherein the surfactant is approximately 0.05% to 50% by weight of said composition.

7. The method of claim 4 wherein the anesthetic is selected from the group consisting of procaine, chloroprocaine, tetracaine, propoxycaine, benzocaine, cocaine, proparacaine, bupivacaine, etidocaine, lidocaine, mepivacaine, prilocaine, dyclonine and promazine.

8. The method of claim 4 wherein the surfactant is selected from the group consisting of monovalent salts, quaternary ammonium salts and polyethylene oxide adducts of fatty alcohols.

9. The method of claim 4 wherein the combination is administered in a pharmaceutically acceptable carrier.

* * * * *